United States Patent [19]

Oliva

[11] Patent Number: 5,022,859

[45] Date of Patent: Jun. 11, 1991

[54] GINGIVAL RECTRACTOR INSTRUMENT

[76] Inventor: Richard A. Oliva, 3318 Club Dr., Los Angeles, Calif. 90064

[21] Appl. No.: 419,142

[22] Filed: Oct. 10, 1989

[51] Int. Cl.$^5$ ............................................... A61C 3/00
[52] U.S. Cl. ................................................... 433/141
[58] Field of Search ........................ 433/141, 136, 146

[56] References Cited
FOREIGN PATENT DOCUMENTS 3539892  5/1987  Fed. Rep. of Germany ...... 433/141

*Primary Examiner*—Cary E. Stone
*Attorney, Agent, or Firm*—Kelly, Bauersfeld & Lowry

[57] ABSTRACT

An improved dental instrument is provided for facilitated placement of retraction cord into the gingival crevice surrounding a tooth. The instrument includes a narrow working tip defining a concave and face adapted for secure, substantially slip-free engagement with retraction cord in the course of packing the cord into the gingival crevice. The retraction cord can thus be placed quickly and easily without significant risk of damage to periodontal attachment tissue at the base of the gingival crevice.

11 Claims, 2 Drawing Sheets

FIG. 5
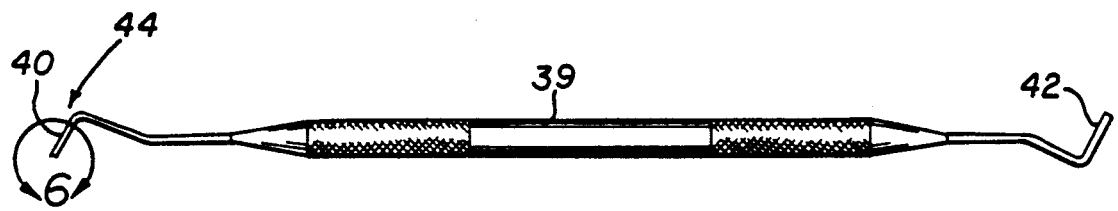
FIG. 7
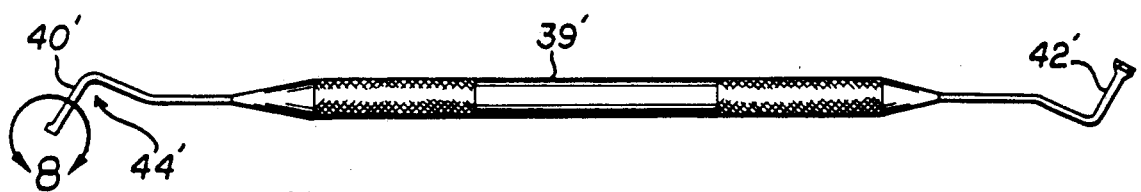
FIG. 6
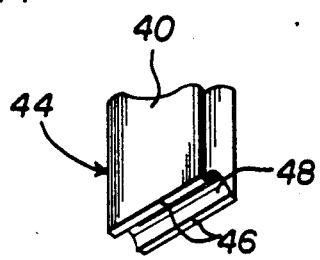
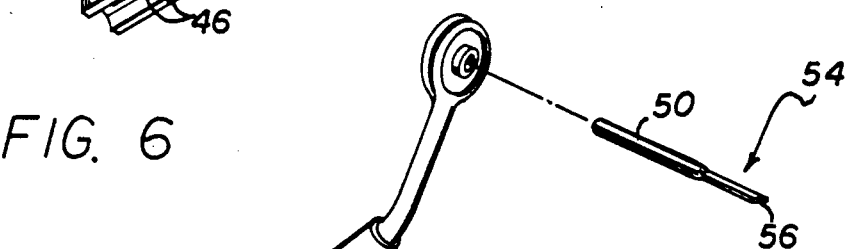
FIG. 9
FIG. 8
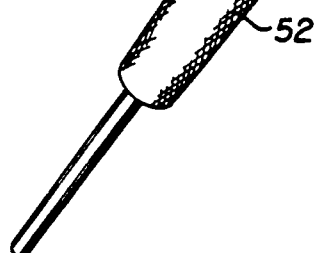
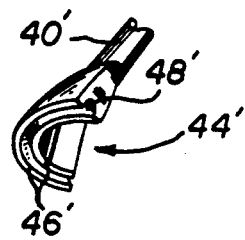

GINGIVAL RETRACTOR INSTRUMENT

BACKGROUND OF THE INVENTION

This invention relates generally to improvements in dental instruments particularly for use in placing retraction cord into the gingival crevice surrounding a selected tooth. More specifically, this invention relates to an improved retractor instrument designed for facilitated placement of retraction cord while preventing or minimizing trauma to adjacent gingival tissue.

Dental restorations such as crowns and bridges are well-known in the art, wherein the exposed crown portion of one or more natural teeth is replaced by a prosthesis formed typically from a gold alloy which may carry an outer shell of porcelain or the like. In accordance with common restorative procedures, the exposed crown portion of the natural tooth is reduced and shaped by drilling to remove damaged portions and to define a suitable prepared base for supporting a prosthetic crown. In this regard, the natural tooth is normally trimmed to a so-called margin disposed slightly below the gum line defined by the surrounding gingival tissue, wherein this margin constitutes a line of separation between cut and uncut portions of the tooth. A moldable and curable impression material such as a selected vinyl-based elastomer is then placed over and about the prepared tooth and allowed to cure, resulting in a resilient mold or impression which is intended to replicate the prepared tooth and surrounding structures within the patient's mouth. This impression is then used according to known casting techniques to produce a custom prosthesis adapted to seat securely onto the prepared tooth and to mate comfortably with adjacent teeth. The prosthesis is installed by cementing onto the prepared tooth in an essentially permanent manner.

The marginal fit between the prosthetic crown and the natural tooth is critical in order to obtain prolonged service life without decay of the prepared tooth in the marginal area. In this regard, to achieve the desired accuracy in marginal detail, it is extremely important for the impression material to flow to and at least slightly beyond the margin of the prepared tooth to insure full reproduction of the marginal area. Unfortunately, since the tooth margin is recessed below the surrounding gum line, the gingival tissue normally blocks flow of the impression material to the desired location. Moreover, trimming of the tooth to the recessed margin is usually accompanied by at least some gingival bleeding around the tooth periphery, wherein the resultant body fluids can also block the desired flow of the impression material.

In the past, these problems have been addressed by the use of retraction cord for temporarily separating the gingival tissue from the margin of the prepared tooth. More specifically, subsequent to tooth preparation and before making the impression, a flexible retraction cord or string is normally placed by packing into the so-called gingival crevice surrounding the prepared tooth. This retraction cord is thus placed slightly below the gum line and functions as a spacer to separate the gingival tissue from the tooth in the marginal area. In many cases, the retraction cord is preimpregnated with a chemical agent that assists in retracting the gingival tissue while reducing the tendency of the tissue to contract immediately when the cord is removed. The retraction cord is then removed immediately prior to making the impression, thereby permitting the impression material to contact and reproduce the marginal area of the tooth.

While the use of retraction cord beneficially enhances the quality of the impression, placement of the retraction cord can be a difficult and time consuming procedure. That is, the gingival tissue normally fits closely about the tooth to define a gingival crest at the gum line. From the gingival crest, the tissue descends alongside the tooth to define a shallow gingival crevice or sulcus, typically having a depth on the order of 1.8 to 2.0 millimeters, the base of which includes periodontal attachment tissue secured to the tooth. The retraction cord must be packed into the gingival crevice to separate the tissue lining the crevice from the tooth, but without disturbing or traumatizing the closely underlying periodontal attachment tissue. In the past, this packing procedure has been performed with a dental instrument having a narrow blunted tip with a squared or convex profile by pressing the instrument tip against the cord to push the cord incrementally into the gingival crevice. More recently, an instrument having a rotatable blunted tip has been proposed. See U.S. Pat. No. 4,396,375. In either case, the blunted tip is intended to avoid trauma to the gingival tissue. However, the blunted tip does not securely engage the retraction cord and thus tends to slip off the cord to contact and damage gingival tissue, particularly such as the periodontal attachment tissue at the base of the gingival crevice. When this attachment tissue is damaged in this manner, the tissue tends to heal with at least some gum line recession resulting in potential exposure of the marginal area between the prosthetic crown and the natural tooth.

There exists, therefore, a significant need for improvements in dental instruments of the type used for placing retraction cord into the gingival crevice surrounding a selected tooth, substantially without damaging the adjacent gingival tissue. The present invention fulfills this need and provides further related advantages.

SUMMARY OF THE INVENTION

In accordance with the invention, an improved gingival retractor instrument is provided for use in packing retraction cord into the gingival crevice surrounding a selected tooth. The instrument includes a narrow profile working tip having a concave end face adapted for relatively secure and stable, substantially slip-free engagement with retraction cord in the course of cord placement into the gingival crevice.

The gingival retractor instrument comprises, in a preferred form, a relatively conventional dental instrument handle of the single or double-ended type. A working tip is formed at one or both ends of the handle, wherein the tip may be suitably angled for ease of access to the marginal area surrounding a selected patient tooth such as a tooth which has been prepared for receiving a prosthetic crown. A distal end or face of the working tip has a relatively narrow profile or width less than about 1.0 millimeter and preferably within the range of about 0.2 to 0.75 millimeter. A shallow concave recess is formed in this distal face to permit and facilitate secure engagement with retraction cord as the cord is tamped and packed into the gingival crevice.

In one preferred form, the distal end face of the instrument working tip has a generally circular geometry with the concave recess formed therein. In another preferred form, the working tip may have an elongated blade configuration with the narrow profile or width and the concave recess running longitudinally at the blade distal end face. In still another embodiment, the working tip may be shaped to define a modified curved blade geometry adapted to conform with nonlinear contours of the gingival crevice. In still other forms, the instrument can be designed for removable attachment to a suitable base handpiece.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention, in such drawings:

FIG. 5 is an elevational view of an instrument embodying one alternative form of the invention;

FIG. 6 is an enlarged fragmented perspective view generally corresponding with the encircled region 6 of FIG. 5;

FIG. 7 is a elevational view of an instrument embodying a further alternative form of the invention;

FIG. 8 is an enlarged fragmented perspective view generally corresponding with the encircled region 8 of FIG. 7; and FIG. 9 is an exploded perspective view illustrating a further alternative form of the invention.

DETAILED DESCRIPTION OF THE PREFERRED EMBODIMENTS

Figure 1:
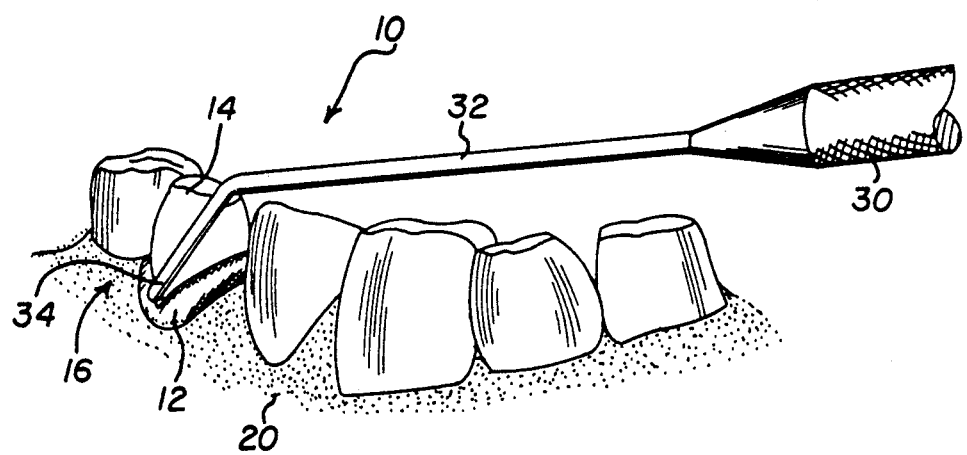
FIG. 1 is a perspective view illustrating placement of a retraction cord into the gingival crevice surrounding a selected tooth, utilizing a gingival retractor instrument embodying the novel features of the invention.

As shown in the exemplary drawings, an improved gingival retractor instrument referred to generally in FIG. 1 by the reference numeral 10 is provided for placement of retraction cord 12 into the gingival crevice surrounding a patient's tooth 14. The instrument 10 includes a specially contoured working tip 16 shaped for secure engagement with the retraction cord 12, substantially without risk of injury or trauma to adjacent gingival tissue.

The improved gingival retractor instrument 10 of the present invention is designed for use in restorative dental procedures, particularly such as the preparation of a natural tooth for receiving a prosthetic crown or the like. In such procedure, a selected tooth 14 is normally reduced and shaped by drilling to define a prepared base for receiving and supporting a prosthetic crown (not shown). Such shaping of the tooth 14 typically involves trimming to a line recessed slightly below the gum line defined by the surrounding gingival tissue 20, wherein this line is normally referred to as the margin and is identified in FIG. 2 by the reference numeral 22. In this regard, the surrounding gingival tissue 20 fits closely about the tooth 14 to define a gum line or gingival crest 24. From the gingival crest 24, the tissue descends alongside the tooth a short distance typically on the order 1.8 to 2.0 millimeter to periodontal attachment tissue 26 which is secured to the tooth. Accordingly, the gingival tissue including the attachment tissue or membrane 26 cooperatively forms a shallow and narrow gingival crevice or sulcus 28 surrounding the tooth.

Figure 2:
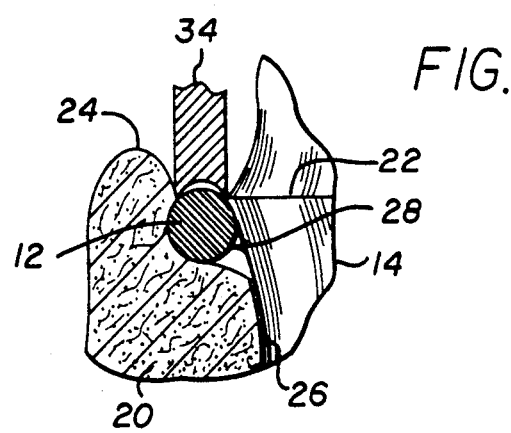
FIG. 2 is an enlarged fragmented vertical sectional view showing engagement of the instrument with the retraction cord in the course of cord placement.
Figure 4:
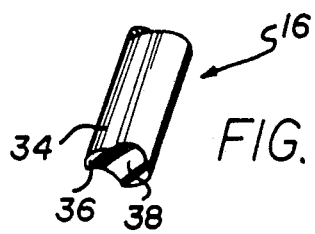
FIG. 4 is an enlarged fragmented perspective view of a working tip for the instrument, generally corresponding with the encircled region 4 of FIG. 3.
Figure 3:
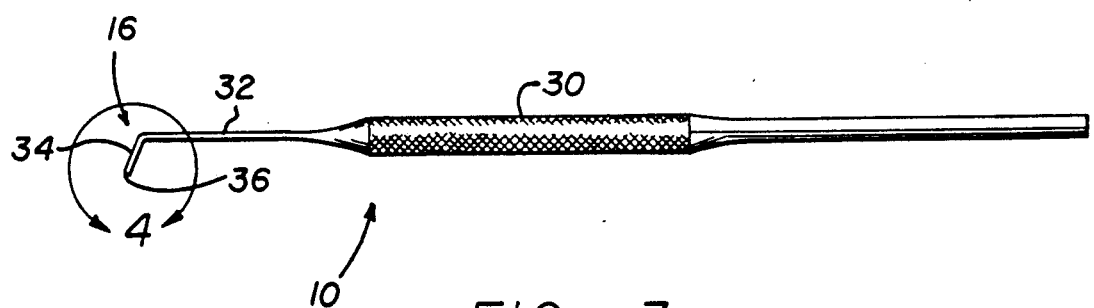
FIG. 3 is an elevational view depicting the instrument in one preferred form.

The retractor cord 12 is packed into the gingival crevice 28, as viewed in FIGS. 1 and 2, for purposes of spacing the gingival tissue from the margin 22 of the prepared tooth 14. More particularly, after tooth preparation, the cord 12 is tamped into the crevice 28 to displace the adjacent tissue in an outwardly direction from the prepared margin. In many instances, the cord 12 includes a chemical agent which reduces the tendency of the tissue to contract immediately upon cord removal. The retraction cord 12 is then removed to expose the margin 22 for a complete and accurate impression to be made of the prepared tooth and surrounding structures. Procedures and materials for making the impression, and subsequent use thereof to produce a custom fit prosthesis, are generally known in the art and thus are not described in further detail herein.

The improved retractor instrument 10 of the present invention facilitates placement of the retraction cord 12 into the gingival crevice 28, while preventing or minimizing risk of injury to the gingival tissue. In one preferred form, as viewed in FIGS. 1-4, the instrument 10 comprises a handle or handpiece 30 having the working tip 16 at one end thereof. The exemplary working tip 16 is shown with an elongated shank 32 projecting from the handle 30 and joined integrally with an angularly set head 34. It will be understood, of course, that the illustrative instrument 10 may be double-ended and include a second working tip at the opposite end of the handle 30, with the second tip typically having a head set at a different angle. In any event, the angled head 34 terminates in a distal or free end face 36 which has a narrow profile sized to fit into the gingival crevice 28 (FIG. 2) substantially without tissue injury. Moreover, in accordance with a primary aspect of the invention, the end face 36 shown in a circular geometry has a concave recess 38 formed therein to extend generally longitudinally across the face.

The recessed face 36 of the instrument working tip is designed for secure and stable engagement with the retraction cord 12 during a cord placement procedure. More particularly, the recessed face 36 is adapted for partially receiving the cord 12 (FIG. 2) such that the tip can be pressed against the cord with little or no risk of the instrument slipping off the cord. As a result, the instrument can be used to press and tamp the cord 12 quickly and easily into position within the gingival crevice. The avoidance of instrument slippage during this procedure reduces the risk of the end face 36 being inadvertently pushed past the cord against the gingival tissue and/or against the periodontal attachment membrane 26. In this regard, while the tissue will normally heal from such instrument inflicted injury, damage to the periodontal membrane can result in tissue recession sufficient to expose the margin 22. After prosthesis installation, such exposure of the margin is undesirable cosmetically and physiologically.

The dimensions of the end face 36 of the instrument working tip 16 are carefully selected for compatibility with retraction cord placement. FIGS. 1-4, illustrate the circular and face 36 having a diametric size of less than 1.0 millimeter and preferably on the order of 0.2 to 0.75 millimeter to fit relatively easily into the gingival crevice 28. The size of the recess 38 is sufficient for secure engagement of the retraction cord 12, having a semicylindrical profile chosen generally to match the external geometry of the cord. This end face configuration has been found effective in safe yet rapid cord placement into the gingival crevice 28 at a desired depth of about 0.7 to 0.8 millimeters below the gingival crest.

FIGS. 5 and 6 illustrate one alternative embodiment of the invention wherein a double-ended instrument handle 39 has appropriately angled heads 40 and 42 at opposite ends thereof. Both heads 40 and 42 define working tips 44 in the form of relatively flat blades each having a narrow width defining an end face 46 with a shallow, longitudinally elongated recess 48 formed therein. The dimensions of the tips 44 generally conform to those previously described with respect to FIGS. 1-4. The blade-type geometry of the working tips is advantageous in pressing retraction cord into relatively flat or straight regions of the gingival crevice.

FIGS. 7 and 8 show another alternative form similar to the embodiment of FIGS. 5 and 6, with counterpart structures being identified by common primed reference numerals. In FIGS. 7 and 8, an instrument handle 39' includes a pair of working tips 44' in the form of curved or arcuate blade segments (FIG. 8). In this version, each tip 44' again includes a narrow end face 46' which incorporates a shallow concave recess 48'. The recess 48' extends from one end of the face 46' to the other, with a width generally conforming with the embodiments previously described. The version of FIGS. 7 and 8 is particularly useful in placing cord segments into curved regions of the gingival crevice, for example, at the corner of a tooth.

A further alternative form of the invention is shown in FIG. 8 wherein a short shaft 50 is provided for detachable mounting into a primary base or handpiece 52, such as a standard power drive drill handpiece or the like. In this form, the shank 50 includes a working tip 54 having a concave end face 56 which may take the form of any one of the configurations shown in FIGS. 1-8. It will be understood, however, that the instrument shank 50 will not normally be rotated during cord placement.

The improved retractor instrument of the present invention thus provides specific utility directed toward improved manipulation of retraction cord 12 during seated placement into the gingival crevice surrounding a tooth. The instrument is designed to securely engage the cord without slipping, thereby preventing or minimizing risk of injury to the gingival tissue.

A variety of further modifications and improvements to the gingival retractor instrument will be apparent to those skilled in the art. Accordingly, no limitation on the invention is intended by way of the foregoing description and the accompanying drawings, except as set forth in the appended claims.

What is claimed is:

1. A gingival retractor instrument, comprising:
  an instrument handle; and
  a working tip formed at one end of said handle and defining a distal end face of circular shape and having a narrow profile less than about 1.0 millimeter in width, said end face further having a recess formed therein.

2. The gingival retractor instrument of claim 1 wherein said recess extends generally across said end face.

3. The gingival retractor instrument of claim 1 wherein said recess is longitudinally elongated.

4. The gingival retractor instrument of claim 1 wherein said end face has a profile within the range of about 0.2 to about 0.75 millimeter.

5. The gingival retractor instrument of claim 1 wherein said handle has a pair of said working tips at opposite ends thereof.

6. A gingival retractor instrument, comprising:
  an instrument handle; and
  a working tip formed at one end of said handle and defining a distal end face of circular shape and having a narrow profile less than about 1.0 millimeter in width, said end face further having an elongated, generally semicylindrical cross section recess formed therein.

7. The gingival retractor instrument of claim 6 wherein said end face has a profile within the range of about 0.2 to about 0.75 millimeter.

8. A gingival retractor instrument, comprising:
  an instrument handle; and
  a blade shaped working tip formed at one end of said handle and defining a distal end face of elongated shape and having a narrow profile less than about 1.0 millimeter in width, said end face further having a recess formed therein to extend longitudinally from one end of said end face to the other.

9. A gingival retractor instrument, comprising:
  an instrument handle; and
  a working tip formed at one end of said handle and defining a distal end face of elongated curved geometry and having a narrow profile less than about 1.0 millimeter in width, said end face further having a recess formed therein extending from one end of said end face to the other.

10. A gingival retractor instrument, comprising:
  an instrument handle; and
  a blade shaped working tip formed at one end of said handle and defining a distal end face of elongated shape and having a narrow profile less than about 1.0 millimeter in width, said end face further having an elongated, generally semicylindrical cross section recess formed therein to extend longitudinally from one end of said end face to the other.

11. A gingival retractor instrument, comprising:
  an instrument handle; and
  a working tip formed at one end of said handle and defining a distal end face of elongated curved geometry and having a narrow profile less than about 1.0 millimeter in width, said end face further having an elongated, generally semicylindrical cross section recess formed therein extending from one end of said end face to the other.

* * * * *